United States Patent [19]

Gordon et al.

[11] 4,048,178
[45] * Sept. 13, 1977

[54] NOVEL N-ALLYL AND N-PROPARGYL BENZMORPHAN DERIVATIVES

[75] Inventors: Maxwell Gordon, Elkins Parks; John J. Lafferty, Levittown, both of Pa.

[73] Assignee: Smith Kline & French Laboratories, Philadelphia, Pa.

[*] Notice: The portion of the term of this patent subsequent to Oct. 3, 1984, has been disclaimed.

[21] Appl. No.: 13,982

[22] Filed: Mar. 10, 1960

[51] Int. Cl.$^2$ .................................................. C07D 221/26
[52] U.S. Cl. ................................. 260/293.54; 424/267
[58] Field of Search ............ 260/294.3, 294.7, 293 D, 260/294.3 A, 285, 293.54

[56] References Cited

U.S. PATENT DOCUMENTS

| 3,345,373 | 10/1967 | Gordon et al. | 260/294 |
| 3,723,440 | 3/1973 | Freter et al. | 260/293.54 |

Primary Examiner—John D. Randolph
Attorney, Agent, or Firm—William H. Edgerton; Alan D. Lourie; Richard D. Foggio

[57] ABSTRACT

N-Allyl-benzmorphan compounds having structures distinguished by having either a 4,5 or 6 carbon containing allyl group at the 2- or N-position or various ether derivatives of the 2'-hydroxy group. The compounds are prepared by alkylation of appropriate N-nor bases and have analgetic antagonist activity particularly pronounced in countering the effects of overdosing. Certain N-acyl-2'-hydroxy-5,9-dimethyl-6,7-benzmorphan intermediates are also disclosed.

3 Claims, No Drawings

NOVEL N-ALLYL AND N-PROPARGYL BENZMORPHAN DERIVATIVES

This invention relates to new 5,9-dimethyl-6,7-benzmorphan derivatives having novel pharmacodynamic activity. More specifically, these compounds have been found to be antagonists of analgetics. The antagonistic effects of these compounds are particularly pronounced against the benzmorphan analgetics such as phenazocine and its analogues. This activity is caused by overdosing, such as respiratory depression.

The compounds of this invention are represented by the following fundamental formula:

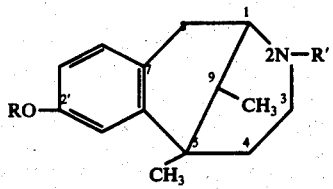

in which R is hydrogen, methyl, acetyl, carbamoyl, benzyl, hydroxyethyl, carbethoxymethyl, dimethylaminoethyl or methoxymethyl; and R' is an allyl or propargyl moiety from 3 to 6 carbon atoms, such as —CH$_2$CH=CH$_2$, —CH$_2$CH=CHCH$_3$, —CH$_2$CH=C(CH$_3$)$_2$,

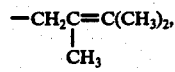

or —CH$_2$C≡CH.

Preferred compounds of this invention are those in which R is hydrogen, methyl or acetyl, and R'is —CH$_2$CH=CH$_2$.

Also included in this invention are various isomers of the above-noted structures, such as cis-trans isomers ("normal" and "iso" series, respectively) at the 5,9 positions, the 2,9 positions, or individual optical isomers which might be separated by fractional crystallization of the diastereoisomeric salts formed, for instance, with d- or l-tartaric acid or D-(+)-α-bromocamphor sulfonic acid. The important iso series of compounds is assumed to have the 9-methyl group in the trans or distal position related either to the 5-methyl group or the 2-N-substituent, however, the absolute configuration of these compounds is not readily apparent at this time.

The bases of this invention may be used as such or in the form of their nontoxic, pharmaceutically acceptable acid addition salts. Such salts are prepared from suitable acids, such as inorganic acids, for instance, hydrochloric, hydrobromic, sulfuric, phosphoric, or sulfamic acid; or organic acids, for instance, acetic, maleic, ethanedisulfonic, glycolic, salicylic and fumaric acids. The acid addition salts are prepared by reacting the base with either one equivalent of acid or preferably an excess in an organic solvent such as ether or an ethanol-ether mixture. Alternatively, an acid salt of the base, say the hydrochloride, can be reacted with a salt such as the ammonium salt of an organic acid in an aqueous mixture to form an insoluble salt by double decomposition.

The compounds of this invention are prepared by reacting the corresponding 5,9-dimethyl-6,7-benzmorphan starting material (U.S. Pat. No. 2,924,603) having a secondary amine function at position 2 with the appropriate reactive allylic halide, such as the chloride, bromide or iodide, usually in the presence of an acid binding agent such as an alkali metal carbonate, hydroxide, etc. The carbonates are preferred such as sodium bicarbonate, potassium bicarbonate, sodium carbonate and potassium carbonate. The reaction is run in an organic solvent in which the reactants are mutually soluble such as a lower alcohol for instance ethanol, methanol or isopropanol. The reaction is preferably run at the reflux temperature of the mixture at from 1 to 24 hours.

The product is isolated by concentrating the filtered molten solution. The residue is taken into an organic solvent in which the inorganic salts in the mixture are not soluble, such as ether or benzene. The dried organic extracts are then worked up to give the desired base.

The 2'-hydroxyl moiety of the compounds of this invention behaves as a normal phenolic hydroxyl in that it can be esterified or etherified with retention of activity. For instance, the acetate can be formed by using an excess of acetic anhydride under standard reaction conditions. The methyl ether can be formed by reaction with diazomethane, preferably before N-alkylation. As a practical matter, the carbon content of the acyl or alkyl portions of these derivatives shall be a maximum of 7. Other acyl moieties exemplary of those included are the benzoate, propionate, isobutyrate, etc. The acetate is preferred.

The other O-ether derivatives can be prepared from 5,9-dimethyl-2'-hydroxy-6,7-benzmorphan by four steps: N-acylation to prepare the N-acyl derivative such as the formyl, carbobenzoxy, carbomethoxy or carbethoxy derivative which are important intermediates included in this invention; O-etherification; hydrolysis of the N-acyl moiety; and alkylation at the N-position.

The following examples are illustrative of the compounds of this invention and the synthetic procedures for preparing these compounds.

EXAMPLE 1

A mixture of 5 g. of 5,9-dimethyl-2'-methoxy-6,7-benzmorphan, prepared by reacting 5,9-dimethyl-2'-hydroxy-6,7-benzmorphan (U.S. Pat. No. 2,924,603) in ethanol with ethereal diazomethane in a closed vessel overnight, evaporating and extracting the methoxy intermediate into ethyl ether, in 110 ml. of ethanol with 2.68 g. of sodium bicarbonate and 2.6 g. of allyl bromide, is stirred under reflux for five hours. The solvent is evaporated. The oily residue is extracted with benzene. The washed and dried benzene extracts are treated with hexane to give a brown gum which is dissolved in acetone and treated with ether to separate the desired 2-allyl-5,9-dimethyl-2'-methoxy-6,7-benzmorphan. The base is dissolved in ethanol and treated with ethereal hydrogen chloride. The crystalline hydrochloride salt melts at 216°–218° C.

EXAMPLE 2

A mixture of 21 g. of 5,9-dimethyl-2'-hydroxy-6,7-benzmorphan, 12.1 g. of allyl bromide, 16 g. of sodium bicarbonate and 350 ml. of ethanol is stirred under reflux for 19 hours. The cooled mixture is filtered and the filtrate concentrated to leave a gum which is extracted with boiling ether. The ether insoluble residue is recrystallized from hexane-ether to give 2-allyl-5,9-dimethyl-2'-hydroxy-6,7-benzomorphan, m.p. 131°–132° C. This compound is dissolved in ethanolic hydrogen chloride and triturated with ether to give the hydrochloride salt.

EXAMPLE 3

A mixture of 0.5 g. of 2-allyl-5,9-dimethyl-2'-hydroxy-6,7-benmorphan in 10 ml. of acetic acid and 15 ml. of acetic anhydride is allowed to stand overnight. It is then warmed on the steam bath briefly, quenched in water, neutralized with carbonate and extracted to give 2'-acetoxy-2-allyl-5,9-dimethyl-6,7-benzmorphan.

EXAMPLE 4

A mixture of 2.1 g. of 5,9-dimethyl-2'-hydroxy-6,7-benzmorphan, 0.8 g. of propargyl chloride, 1 g. of sodium carbonate in 75 ml. of ethanol is heated at reflux for 24 hours. Working the reaction up as in Example 2 gives 5,9-dimethyl-2'-hydroxy-2-propargyl-6,7-benzmorphan. The base (500 mg.) in benzene is reacted with sulfuric acid to give the sulfate salt.

EXAMPLE 5

A mixture of 2.29 g. of 5,9-dimethyl-2'-methoxy-6,7-benzmorphan, 0.89 g. of crotonyl iodide, 1.2 g. of potassium carbonate in 100 ml. of ethanol is heated at reflux for 12 hours. Working the reaction up as described in Example 1 gives 2-crotonyl-5,9-dimethyl-2'-methoxy-6,7-benzmorphan and its hydrochloride salt.

EXAMPLE 6

A mixture of 4.5 g. of 5,9-dimethyl-2'-hydroxy-6,7-benzmorphan in 150 ml. of methyl formate is heated at reflux for four days. The mixture is evaporated and the residue washed with water and then ethyl ether. The residue remaining is crude 5,9-dimethyl-2-formyl-2'-hydroxy-6,7-benzmorphan.

EXAMPLE 7

A mixture of 2.5 g. of 5,9-dimethyl-2-formyl-2'-hydroxy-6,7-benzmorphan (Example 6), 0.5 g. of sodium carbonate, 1.3 g. of benzyl chloride in 150 ml. of toluene is heated at reflux for several hours. The solution is washed with water, then evaporated to leave 2'-benzyloxy-5,9-dimethyl-2-formyl-6,7-benzmorphan. This residue is warmed for an hour in methanolic hydrogen chloride. The mixture is evaporated to give the free base.

EXAMPLE 8

A mixture of 3 g. of 2'-benzyloxy-5,9-dimethyl-6,7-benzmorphan (Example 7), 0.4 g. of sodium bicarbonate, 0.8 g. of 3,3-dimethylallyl bromide in 150 ml. of ethanol is stirred under reflux for several hours. The reaction mixture is worked up as in Example 1 to give 2'-benzyloxy-5,9-dimethyl-2-(3',3'-dimethylallyl)-6,7-benzmorphan.

EXAMPLE 9

A mixture of 2.25 g. of 5,9-dimethyl-2'-hydroxy-6,7-benzmorphan, 0.75 g. of ethyl chloroformate, 0.7 g. of potassium carbonate and 175 ml. of methanol with a few drops of water is heated at reflux for two days. The reaction mixture is evaporated and the residue washed with ether. The ether insoluble residue is the N-carbethoxy analogue. A mixture of 1.4 g. of this compound, 0.2 g. of sodium hydroxide, 0.63 g. of ethylene bromohydrin and 150 ml. of benzene is heated at reflux for two hours. Working up as in Example 7 gives 2-carbethoxy-5,9-dimethyl-2'-($\beta$-hydroxyethoxy)-6,7-benzmorphan. This compound (1.7 g.) is hydrolyzed as in Example 7, then reacted with allyl chloride and sodium bicarbonate in ethanol as in Example 1 to give 2-allyl-5,9-dimethyl-2'-($\beta$-hydroxyethoxy)-6,7-benzmorphan.

EXAMPLE 10

A mixture of 4.5 g. of 5,9-dimethyl-2'-hydroxy-6,7-benzmorphan, 1.4 g. of methyl chloroformate, 1.4 g. of potassium carbonate and 250 ml. of methanol is heated at reflux for 3 days. Working up as in Example 9 gives the N-carbomethoxy analogue. This compound (2.6 g.) is reacted with 0.8 g. of methyl chloromethyl ether and 0.7 g. of potassium carbonate in benzene as in Example 7 to give 2-carbomethoxy-5,9-dimethyl-2'-methoxymethoxy-6,7-benzmorphan. After hydrolysis in methanolic hydrogen chloride of 2 g. of this compound as in Example 7 and alkylation of the residue therefrom with 0.9 g. of propargyl bromide as in Example 8, 5,9-dimethyl-2'-methoxymethoxy-2-propargyl-6,7-benzmorphan is obtained.

EXAMPLE 11

Substituting carbobenzoxyl chloride in molar equivalent amount for the ethyl chloroformate in Example 9 gives the N-carbobenzoxy analogue. Substituting ethyl bromoacetate for benzyl chloride in Example 7 gives 2-carbobenzoxy-2'-carbethoxymethoxy-5,9-dimethyl-6,7-benzmorphan. Hydrolysis in methanolic hydrogen chloride gives the base which (1.2 g.) is then reacted with a slight excess of 2,3,3-trimethylallyl bromide with sodium carbonate in ethanol to give 2'-carbethoxymethoxy-5,9-dimethyl-2-(2',3',3'-trimethylallyl)-6,7-benzmorphan. This compound (200 mg.) is dissolved to ethanolic hydrogen bromide and triturated with ether to give the hydrobromide salt.

EXAMPLE 12

A mixture of 0.6 g. of 2-allyl-5,9-dimethyl-2'-hydroxy-6,7-benzmorphan in benzene is reacted with an ethereal solution containing 0.3 g. of carbamyl chloride. Evaporation of the solvent gives the 2'-urethane derivative.

EXAMPLE 13

Substituting a molar equivalent amount of 2-dimethylaminoethyl bromide for the ethylene bromohydrin of Example 9 gives 2-allyl-5,9-dimethyl-2-dimethylaminoethoxy-6,7-benzmorphan.

EXAMPLE 14

A mixture of 1 g. of iso-5,9-dimethyl-2'-hydroxybenzmorphan, 0.6 g. of allyl chloride, 0.8 g. of sodium carbonate and 200 ml. of ethanol is stirred under reflux for 19 hours. The cooled mixture is worked up as in Example 2 to give iso-2-allyl-5,9-dimethyl-2'-hydroxy-6,7-benzmorphan.

What is claimed is:
1. A chemical compound having the following formula:

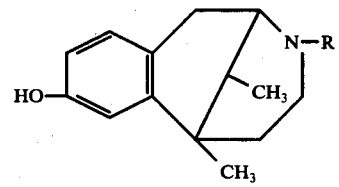

In which R is a member selected from the group consisting of carbethoxy, formyl, carbomethoxy and carbobenzoxy.

2. 5,9-Dimethyl-2-formyl-2'-hydroxy-6,7-benzmorphan.

3. 2-Carbethoxy-5,9-dimethyl-2'-hydroxy-6,7-benzmorphan.